United States Patent [19]

Kempe

[11] Patent Number: 5,750,672
[45] Date of Patent: May 12, 1998

[54] ANHYDROUS AMINE CLEAVAGE OF OLIGONUCLEOTIDES

[75] Inventor: Tomas Kempe, Bowie, Md.

[73] Assignee: Barrskogen, Inc., Bowie, Md.

[21] Appl. No.: 755,398

[22] Filed: Nov. 22, 1996

[51] Int. Cl.$^6$ .............................. C07H 1/02; C07H 21/00
[52] U.S. Cl. ................... 536/25.31; 536/23.1; 536/24.3
[58] Field of Search ........................... 536/25.4, 23.1, 536/25.31, 24.3

[56] References Cited

U.S. PATENT DOCUMENTS

| | | | |
|---|---|---|---|
| 5,348,868 | 9/1994 | Reddy et al. | 435/91.1 |
| 5,686,599 | 11/1997 | Tracz | 536/25.31 |

OTHER PUBLICATIONS

Reddy et al Tetrahedron Letters, 35(25):4311–4314.

*Primary Examiner*—Gary L. Kunz
*Attorney, Agent, or Firm*—Frederikson & Byron, P.A.

[57] ABSTRACT

A method for recovering synthesized oligonucleotides from a solid support that includes the step of incubating the solid support with an anhydrous amine reagent under conditions suitable to cleave and deprotect the oligonucleotide. The cleaved and deprotected oligonucleotide will be substantially insoluble in the reagent and/or will exhibit preferential affinity for the support. Reagent kits for use in such a method, and cleaved, deprotected oligonucleotides prepared by means of such a method are provided.

19 Claims, No Drawings

1

ANHYDROUS AMINE CLEAVAGE OF OLIGONUCLEOTIDES

TECHNICAL FIELD

The present invention relates to solid phase oligonucleotide synthesis, and in particular to methods for the cleavage and deprotection of synthetic oligonucleotides, such as DNA or RNA molecules, by the use of reagents such as organic amines.

BACKGROUND OF THE INVENTION

The principle of solid phase oligonucleotide synthesis traces its history to work of Merrifield, Khorana and others in the 1950's and 1960's. The development of automated synthetic methods over the past decade has had a major impact in the field of molecular biology and biological chemistry. The stepwise synthesis of deoxyoligonucleotides generally involves the formation of successive diester bonds between 5'-hydroxyl groups of bound nucleotide derivatives and the 3'-hydroxyl groups of a succession of free nucleotide derivatives.

The synthetic process typically begins with the attachment of a nucleotide derivative at its 3'-terminus by means of a linker arm to a solid support, such as silica gel or beads of borosilicate glass packed in a column. The ability to activate one group on the free nucleotide derivative requires that other potentially active groups elsewhere in the reaction mixture be "protected" by reversible chemical modifications. The reactive nucleotide derivative is a free monomer in which the 3'-phosphate group has been substituted, e.g., by dialkylphosphoramidite, which upon activation reacts with the free 5'-hydroxyl group of the bound nucleotide to yield a phosphite triester. The phosphite triester is then oxidized to a stable phosphotriester before the next synthesis step.

The 3'-hydroxyl of the immobilized reactant is protected by virtue of its attachment to the support and the 5'-hydroxyl of the free monomer can be protected by a dimethoxytrityl ("DMT") group in order to prevent self-polymerization. A methyl group is usually used to protect the hydroxyl of the 3-phosphate. Additionally, the reactive groups on the individual bases are also protected. A variety of chemistries have been developed for the protection of the nucleoside exocyclic amino groups. The use of N-acetyl protecting groups to prepare N-acetylated deoxynucleosides has found wide acceptance for such purposes.

After each reaction excess reagents are washed off the columns, any unreacted 5'-hydroxyl groups are blocked or "capped" using acetic anhydride, and the 5'-DMT group is removed using 80% acetic acid to allow the extended bound oligomer to react with another activated monomer in the next round of synthesis. Finally, the fully assembled oligonucleotide is cleaved from the solid support and deprotected, to be purified by HPLC or some other method. The useful reagents and conditions for cleavage depend on the nature of the linkage. With ester linkages, as are commonly provided by linkage via succinyl groups, cleavage can occur at the same time as deprotection of the bases, by the use of concentrated aqueous ammonium hydroxide.

Synthetic methodologies that were in common use a decade ago, such as the phosphodiester method, are now largely obsolete. Today almost all synthetic oligonucleotides are prepared by solid phase phosphoramidite techniques. See generally T. Brown and D. Brown, "Modern Machine-Aided Methods of Oligonucleotide Synthesis", Chapter 1, pp. 1–24 in *Oligonucleotides and Analogues, A Practical Approach*, F. Eckstein, ed., IRL Press (1991).

The reagent most commonly used for the cleavage/deprotection of synthetic oligonucleotides is the concentrated aqueous ammonium hydroxide method. See, e.g., Protocol 5 of Brown and Brown, cited above. It can be seen that the time required for an ammonium hydroxide incubation is usually on the order of many hours, and generally involves heated incubation overnight. Regular cleavage and deprotection protocols using aqueous reagents are typically performed in a two step procedure where the cleavage of the nucleotide from the solid support is first achieved, followed by deprotection of the base labile protecting groups in a solution that has solubilized the oligonucleotide.

The cleavage and deprotection of oligonucleotides can be performed under non-solution conditions as well, for instance, using gas phase reagents in the manner described in Applicant's U.S. Pat. No. 5,514,789. The gas phase reaction is completed on the solid support using gaseous reagent at a temperature and time sufficient to cleave or deprotect the oligonucleotide. Upon completion, the oligonucleotide can be eluted from the support, e.g., with water or buffer. Optionally, the cleaved and deprotected oligonucleotide can be used in situ, that is, directly on the support and without an evaporation or precipitation step.

Automated oligonucleotide synthesis typically concludes with the newly synthesized oligonucleotide still covalently attached to the support. Any remaining reagents have been washed from the column by the use of a solvent such as acetonitrile. Typically, the wash solvent is then either dried from the support, and the support resuspended in cleavage/deprotection buffer, or the solvent containing the support is poured from the column and processed separately (e.g., by DMT purification).

Commercial oligonucleotide synthesizers can be retrofitted to employ a gas phase process, e.g., by incorporating a gas chamber and related controls and tubing. Presently, however, the gas phase process is typically performed in a separate, stand alone gas chamber. Ideally, oligonucleotide synthesizers having a gas phase cleavage and deprotection feature will be available in the future. Until that time, it would be particularly advantageous to be able to use existing oligonucleotide synthesizers for an automated cleavage, deprotection and recovery routine.

SUMMARY OF THE INVENTION

The present invention provides a rapid, solution phase method for the recovery of newly synthesized oligonucleotides such as DNA or RNA. The method permits a variety of sequential steps, including cleavage, deprotection, desalting and/or recovery, each of which can be performed in the same reaction vessel, and optionally, on the synthesizer itself. In turn, the method permits the user to extend the automated steps performed on the synthesizer to include DMT purification. Alternatively, the method permits the automated cleavage and deprotection of an oligonucleotide, and the recovery of that oligonucleotide in the same reaction vessel, to be used in situ or later eluted.

In a preferred embodiment, Applicant has discovered a method that employs an anhydrous amine reagent to cleave and deprotect a newly synthesized oligonucleotide. The reagent comprises an anhydrous amine such as a primary amine, secondary amine or cyclic secondary amine used neat or dissolved in an organic solvent that not substantially dissolve an oligonucleotide from a solid support. While not intending to be bound by theory, it appears that in each case either the oligonucleotide is substantially insoluble in the reagent of the present invention and/or the oligonucleotide exhibits preferential affinity for the support.

Applicant has discovered that the cleavage/deprotection reagent can be removed from the reaction vessel in order to preferentially leave the oligonucleotide retained upon the support itself. There, the oligonucleotide can be used in situ in a variety of ways, or can be further processed or recovered by other techniques.

The anhydrous amine method of the present invention provides a number of advantages over conventional recovery protocols, such as those that rely on the use of aqueous phase cleavage/deprotection reagents. In particular, according to the present method the oligonucleotide can be recovered in a buffer without the need for evaporation or precipitation steps. This can translate into substantial advantages, both in terms of easier recovery protocol, as well as an increase in yield.

The method of this invention can also be adapted to a commercial oligonucleotide synthesizer by the use of existing or added reservoirs and tubing systems for the delivery of the anhydrous and other reagents. In this respect, the invention also provides an anhydrous amine reagent provided in a premeasured and prepackaged form, either for direct use on a conventional synthesizer or for a manual method.

Applicant has discovered a number of other advantages as well. One such advantages is the speed and convenience of obtaining user-ready oligonucleotides that can be achieved by directly resuspending the cleaved product in a buffer after the removal of amine reagent, i.e., without the additional recovery steps of precipitating product or evaporating reagent. Yet another advantage is the opportunity to simultaneously process multiple samples of oligonucleotides made in picomolar ("pmolar") scale, for example in the form of microplates having 96 reaction wells.

In addition to advantages in recovery time and yield, the elimination of an evaporation step provides an added advantage in the form of a reduced potential for cross-contamination between samples. Conventional evaporation techniques, e.g., those in which liquid recovery reagents are removed by the use of heating and/or vacuum, have a tendency to create "bumping" or splashing of such volatile reagents as liquid ammonium hydroxide.

The process provides an alternative to the conventional ammonium base procedures described above as well as the gas phase method described in copending application No. PCT/US93/03123. The process of the present invention can lower the total processing time for newly synthesized oligonucleotide to on the order of one hour or less, and preferably thirty minutes or less, without the need for additional equipment or sacrifice in the quality of the resultant oligonucleotide.

DETAILED DESCRIPTION

In a preferred embodiment the invention provides a method for recovering synthesized oligonucleotides from a solid support, the method comprising the steps of (1) providing a solid synthetic support having synthesized oligonucleotides bound thereto, and (2) incubating the solid support with an anhydrous amine reagent under conditions suitable to cleave and deprotect the oligonucleotide. The cleaved and deprotected oligonucleotide will be substantially insoluble in the reagent and/or will exhibit preferential affinity for the support.

The preferred method involves the further steps of (3) removing the solution phase reagent in a manner that permits the cleaved and deprotected oligonucleotide to be preferentially retained on the support, and optionally, (4) washing the support. Finally, the preferred method can include the final step (5) of recovering the oligonucleotide from the support, for instance using a polar solvent or aqueous wash, or using the recovered oligonucleotide in situ.

In one aspect the present invention provides a method for recovering newly synthesized oligonucleotides using an anhydrous amine as the cleavage/deprotection reagent. In another aspect, the invention relates to an anhydrous amine reagent, per se, packaged and suitable for use in such a method. In yet another aspect, the invention provides an oligonucleotide that has been cleaved and deprotected by the use of such a reagent. In still another aspect, the invention relates to a combination comprising a cleaved and deprotected oligonucleotide adsorbed to a support material. Finally, the invention provides for the use of such an oligonucleotide, either in the course of further purification or the its use in situ in the course of one or more further biochemical reactions.

Synthetic oligonucleotides.

The preferred method involves a first step of providing a solid synthetic support having synthesized oligonucleotides bound thereto. In such a preferred embodiment, the newly synthesized oligonucleotide is the synthetic product of a solid phase synthesis protocol such as the cyanoethyl phosphoramidite protocol and is protected by base labile protecting groups that are susceptible to cleavage by an alkylamine.

Suitable protecting groups for use in the present invention are base labile groups, including acyl groups (e.g., acetyl, benzoyl, isobutyryl, phenoxyacetyl groups) and amidine groups (e.g., formamidine and dimethylamidine). Such protecting groups can be removed and converted to soluble derivatives such as amides by the use of anhydrous amines of the present invention. In this form, the removed organic groups will generally be soluble in the amine reagent. The removal of the amine reagent will therefore serve to remove these amides, thereby "desalting" both the oligonucleotide product and the solid support.

In a particular preferred embodiment, the solid support is provided either in the form of a conventional synthesis column for use on an automated synthesizer, or in the form of 96 well microtiter plate of the sort commonly used in immunological assay protocols. Such supports are typically prepared from such materials as polystyrene, controlled pore glass, glass beads, PVDF membranes, and the like, and those skilled in the art will appreciate the manner in which they can be manufactured to include support surfaces that are particularly suited to the synthesis of oligonucleotides.

The solid support can also be provided in the form of a 96 well microtiter plate type, of the sort that more commonly is used in immunological assay protocols. Multiple sample processing using such microplates can also be performed using regular scale synthesis, e.g., in the range of about 30 nmol to about 200 nmol of product per well. The process will thus provide for the convenient cleavage and deprotection of up to 96 samples, in such amount per plate.

Each well of a 96 well microtiter plate can be fitted, e.g., with a frit or a depth filter at the bottom of the plate, in order to retain a loose support, e.g., in the form of a membrane or particulate material. The depth filter, in turn, can itself be functionalized, for instance, with nucleoside.

The oligomer is typically attached to the support with an ester bond between the 3'-hydroxyl group of DNA or RNA to the support. The monomer building blocks for the synthesis are typically protected at the 5'-end with labile protecting groups typically sensitive to acids such as the dimethoxytrityl group (DMT-). The side chains of the nucleosides are protected with base labile protecting groups such as acetyl derivatives, benzoyl derivatives, phenoxyacetyl derivatives, formamidine derivatives or any group that is suitable in a solid phase oligonucleotide synthesis protocol that can be removed with an anhydrous amine reagent without affecting the purity of the final product. The reactive phosphoramidite cyanoethyl group is used to generate internucleotide phosphite bond and subsequently oxidized to a stable phosphotriester bond.

When phosphoramidites other than the cyanoethyl protected amidites are used, a deprotection protocol that is appropriate is being used. For example, when the classical methoxy protecting group is used the removal of that groups is first performed in order to avoid alkylation of the nucleoside bases. Thus, the first step in removing methoxy groups is done by incubating the solid support in a thiol reagent, e.g., thiophenol in order to first remove the methyl group, followed with an optional washing with a solvent that remove the excess thiol, followed by the procedure outlined for the use of nonaqueous amine reagents above.

The oligonucleotide of the present invention can be of any desired type and size and can be "bound" by any means or combination of means suitable for its intended use, e.g., through chemical bond attachment, affinity attachment, ion exchange attachment, or through size exclusion attachment to the support. Columns can contain solid matrices in the form of, for instance, particles (such as solid, porous, or hollow beads), permeable or impermeable membranes, stable emulsified droplets, and solid support surfaces in any desired configuration. For purposes of the present invention, it is only required that the method of attachment be susceptible to cleavage (e.g., disengagement from the support) using the presently claimed reagents and method.

Anhydrous amine reagent.

The invention involves the further step of incubating the solid support with an anhydrous amine reagent under conditions suitable to cleave and deprotect the oligonucleotide. The cleaved and deprotected oligonucleotide will be substantially insoluble in the reagent and/or will exhibit preferential affinity for the support.

The term "anhydrous amine", as used herein, will generally refer to an amine reagent capable of cleaving and/or deprotecting a synthetic oligonucleotide, the reagent preferably being one in which the cleaved oligonucleotide is substantially insoluble. The amine function is preferably either a primary or secondary amine, having the ability to nucleophilically attack a base labile protecting group on the nucleotide. Such amine reagents generally do not contain water, as compared to the term "nonaqueous" amines, which will be used to describe amine reagents that contain a prootic solvent other than water.

In general, any noninterfering organic or inorganic amine reagent can be used at temperatures and under conditions that do not undesirably alter the content or composition of the final product. Large scale processing of DNA/RNA is also facilitated since it is now possible to eliminate the need to use large volumes of concentrated ammonium hydroxide in the cleavage and deprotection steps. The reactivity of the cleavage reagent itself can also be enhanced if the reaction is performed in a chamber suited for elevated pressure and/or temperatures associated with the vapor pressure of the amine reagent with or without solvent. Optionally, as an additional step, the support can be washed with on organic solvent in the same chamber in order to remove residual amine reagent and provide a neutral pH.

Preferably, the reagent is selected from the group consisting of primary alkylamines, secondary amines, and cyclic amines, as well as combinations thereof. Suitable primary alkylamines include methylamine, ethylamine, propylamine, butylamine, pentylamine, hexylamine, heptylamine, and isomers thereof. Suitable secondary amines include dimethylamine, ethylmethylamine, diethylamine, methylisopropylamine, and diisopropylamine. Suitable cyclic amines include ethyleneimine, pyrrole, pyrrolidine, cyclohexylamine and ring substituted derivatives, benzylamine derivatives, primary and secondary with substituents optionally at the aromatic ring, diamines such as ethylenediamine and tetraamines such as ethylenetetraamine, amine derivatives with other functional groups that are inert to the base, such as ether linkages, sulfur linkages, nitro groups, cyanide groups for the purpose of enhancing a specific solid phase - liquid phase reaction in the cleavage or deprotection of oligonucleotide or RNA attached to a support.

One or more noninterfering solvents or cosolvents can be used in the cleavage and deprotection reaction with the amine reagent. The term "noninterfering", when used in this sense, refers to a solvent or cosolvent that does not unduly affect the use of the anhydrous amine for its intended purpose. Such solvents are generally nonpolar but prootic solvents that do not substantially dissolve the oligonucleotide from the support can be used as well.

When the amine component is gaseous at room temperature, such as methylamine, ethylamine and dimethylamine, the amine can be dissolved in a nonpolar organic solvent, e.g., at a concentration range of between about 1% and about 50%, by volume, based on the volume of the final reagent. When the amine is liquid at room temperature the amine can optionally be dissolved in a nonpolar organic solvent but is preferably used without solvent. Solid alkylamines (e.g., long chain alkylamines such as decylamine, undecylamine, and the like) are preferably dissolved in a nonpolar organic solvent, e.g., at a concentration of between about 1% and about 75%, and preferably between about 20% and about 40%, based on the weight of the final reagent. Examples of suitable nonpolar solvents include, but are not limited to organic solvents such as tetrahydrofuran, acetonitrile, hydrocarbons and the like.

The amine reagent can be delivered into the column and the column incubated under conditions suitable to perform the cleavage/deprotection reaction. Optionally, the column can be heated to increase the rate of reaction. Preferably, using an oligonucleotide prepared with labile protecting groups, such as phenoxyacetyl protecting groups, cleavage and deprotection can be performed at room temperature within about 30 minutes or less, and preferably within about 15 minutes or less.

Using a 96 well format, as described herein, the incubation step of the invention can be performed in any suitable manner, e.g., by pipetting the amine reagent into each well manually or through a robotics pipetting station which operates in the 96 well format. The reagent can be removed and washed off by any suitable method, such as by vacuum, pressure, or centrifugation. In an alternative embodiment, the support can itself be transferred to a suitable container, or can itself be used to form a container. The final cleavage and deprotection of the oligonucleotide is then performed by the introduction of anhydrous amine reagent, preferably in a sealed container. This process allows multiple cleavage deprotection steps to be performed simultaneously on an almost unlimited number of samples.

Removing solution phase.

The invention further involves the step of removing the solution phase reagent in a manner that permits the cleaved and deprotected oligonucleotide be preferentially retained on the support, and optionally, washing the support.

Once cleavage and deprotection has been completed, the amine reagent can be removed by any suitable means, e.g., purging the column with gas, applying a vacuum to draw off the reagent, or delivering an additional wash volume of inert nonpolar solvent, all under conditions suitable to permit the oligonucleotide to remain on the support. Examples of suitable nonpolar wash solvents include tetrahydofuran (THF), diethylether, acetonitrile, petroleum ether, chlorinated hydrocarbons and combinations thereof. Preferably, the wash solvent is itself miscible in an aqueous system, thereby permitting residual wash solvent to form a single phase when the oligonucleotide is subsequently eluted.

Preferably, the removal of the amine reagent and any subsequent wash solvent will serve to also remove any amide derivatives generated during the deprotection step. These amide derivatives, such as benzamides and phenoxyacetylamides are generally soluble in the alkylamine derivatives used in the amine reagent or in the solvents used when diluted amine reagents are preferred. Prootic solvents can be used in combination with the amine reagent but caution must be taken to ensure that the combination does not dissolve the oligonucleotide from the support, resulting in loss of product.

Recovering and/or using cleaved, deprotected oligonucleotide.

Finally, the preferred method can include the step of recovering the oligonucleotide from the support, for instance using a polar solvent or aqueous wash, or using the recovered oligonucleotide in situ.

In one preferred embodiment, after removal of the amine reagent, the cleaved and deprotected oligonucleotide can be solubilized and removed from the support using an aqueous solution. It can then be eluted from the solid support and used directly in molecular biology experiments without the need for an evaporation step. For instance, the cleaved, deprotected oligonucleotide can be resuspended and recovered in a sodium hydroxide solution. After elution from the support, the oligonucleotide can thereafter be precipitated in order to convert the product to the sodium salt, e.g., using the method and reagents described in Applicants co-pending application Ser. No. 08/435/526, the disclosure of which is incorporated herein by reference.

In the event the oligonucleotide requires additional purification, several alternative approaches are provided by the method of this invention. For instance, the oligonucleotide can be eluted from the support as a DMT sequence for further cartridge purification or HPLC purification following conventional protocols. Alternatively, the DMT can be purified using a modified cartridge protocol, if the support material (such as polystyrene) is sufficiently lipophilic. After washing off the amine reagent, a solution of aqueous acetonitrile (e.g., 1–5%) can be added in order to wash off failure sequences that do not contain the DMT-group. The DMT groups are then removed with an acid, typically 1–2% trifluoroacetic acid in water. The acid is washed off with water and the final DMT purified oligonucleotide is eluted using a stronger solvent, such as 5% to 20% acetonitrile in water. The solution can be concentrated to recover the oligonucleotide.

The oligonucleotide may also be converted to the sodium salt if its intended use is in antisense oligonucleotide experiments. A reagent combination as described in copending application (Ser. No. 08/435,526) can be used. In particular, the synthetic oligonucleotide can be recovered in the form of the sodium or potassium salt by a method that comprises the steps of:

(a) providing the composition comprising synthetic oligonucleotides in the form of the ammonium salt.

(b) combining the salt composition with a basic NaOH or KOH reagent solution suitable to cause the conversion of the ammonium salt to the form of a sodium or potassium salt, (c) mixing the basic solution with a precipitating solvent reagent comprising between about 0.5% and 5% acetic acid in an alcohol selected from the group consisting of 2-propanol, propanol, ethanol, butanol, and ethanolamine under conditions suitable to precipitate the oligonucleotide from the combined solution within about 10 minutes incubation at room temperature.

Optionally the oligonucleotide can be purified on the solid support resin through affinity chromatography or be purified on a separate support material such as solid support used in HPLC chromatography.

The method of this invention can also be used to enrich and recover oligonucleotide sequences complementary to an immobilized sequence, e.g., for the purpose of selectively removing such sequences from a solution. In one such approach, infrequent sequences can be enriched from specimen for diagnostic purposes. A target sequence enriched in this manner can, in turn, be amplified and characterized, for example, by the use of a PCR (polymerase chain reaction) process. The present invention also has processing applications, since the oligonucleotide can be recovered, packaged and shipped in situ on the support and in recoverable and/or biologically active form.

Applications.

The present invention provides a rapid process for the cleavage and deprotection and recovery of user-ready oligonucleotides. The process provides an alternative to the conventional procedures using aqueous ammonium hydroxide and aqueous methylamine. By use of the method and reagents of the invention synthesized oligonucleotide can be processed within a time frame that has not heretofore been available to those in the field.

Furthermore, the reagent can be used on existing oligonucleotide synthesizers, allowing them to provide a greater level of automation. An anhydrous amine reagent of the present invention can be provided in the form of an easy-to-use kit containing the reagent in premeasured and prepackaged form, e.g., packaged in a container of the type often used for "ancillary" reagents. Without the need for mixing or further handling, is adapted to be attached to a conventional synthesizer for use in performing the method described herein. The reagent can be packaged in any of a variety of containers, dimensioned to be used on the synthesizer and having a cover (e.g., screw cap or septum cap) suitable for use. The container is preferably packaged with purified anhydrous amine reagent under inert conditions, virtually eliminating moisture and oxygen contamination, and is labeled and color coded for quick and easy placement on a synthesizer.

For the manufacture of a kit for manual application, the premeasured, prepackaged anhydrous amine reagent is preferably packaged (e.g., in a bubble pack) in the form of a plurality of individually packaged identical containers, with a corresponding number of disposable syringes. After synthesis, the reaction vial can be removed, and the syringe can be inserted to deliver the anhydrous amine.

In order to speed up the cleavage and deprotection on the machines, a heating device can be added, if the protecting groups are sufficiently stable, in order to heat the oligonucleotide synthesis columns containing the amine reagent.

In conventional RNA synthesis, the RNA product is typically first cleaved from the column using aqueous reagents (e.g., aqueous ammonium hydroxide), after which the phosphate and base labile protecting groups are removed by heating the solution. As a final step, the ammonium hydroxide itself needs to be removed by evaporation and a fluoride reagent is then used to remove the 2'-silyl protecting group and provide the final product.

Using the method of the present invention, one can achieve the same result in a manner that provides several options as well as a considerable savings of time and effort. For instance, the RNA can be cleaved and its phosphate and base labile protecting groups deprotected by the use of an anhydrous amine reagent in the manner described herein. The remaining RNA, with its 2'-hydroxyl groups still protected (e.g., by 2'-silyl groups) can then be fully deprotected in situ (e.g., using an anhydrous flouride reagent). Optionally, this partially deprotected RNA can be eluted and fully deprotected in the aqueous phase using a conventional fluoride reagent.

Formats.

In another embodiment the invention provides an apparatus for recovering synthesized oligonucleotides from a solid support, the apparatus comprising a container having anhydrous amine reagent, a sealable chamber for retaining the solid support and incubating the support the reagent, and delivery means for transferring the reagent to the chamber. The final product can be eluted from the support in an aqueous buffer or water, e.g., in an automated fashion using an apparatus fitted with a collection vial, or manually with the use an apparatus as described in U.S. Pat. No. 5,496,473.

The solid/liquid phase reaction described herein offers a workable method for synthesizing pmolar amounts of oligonucleotide on multiple well plates, and for incorporating new approaches as well. Particularly with microplates, for instance, approaches (including robotic equipment and associated software) have been developed for various handling, delivery, sampling, and reading procedures necessary for fully automated use. Oligonucleotide synthesizers can be designed to incorporate the microplate technology, in order to permit rapid cleavage and deprotection according to the method described herein.

Applied BioSystems, Inc., for instance, has recently introduced an instrument capable of simultaneously synthesizing and processing 48 samples, including cleavage, deprotection and recovery steps using aqueous ammonium hydroxide. The cleaved oligonucleotide is collected for a deprotection step, and the deprotected oligonucleotide is reintroduced onto the column for a cartridge purification protocol followed by elution, quantification and evaporation of the oligonucleotide. An anhydrous amine reagent, of the type disclosed herein, can be adapted for use on such an instrument in order to provide greater efficiency, particularly in the microtiter format.

The cleavage or deprotection with anhydrous amines can be performed after partial cleavage and deprotection has been performed using the gas phase reagents described in U.S. Pat. No. 5,514,789. After the gas phase treatment to partially cleave an/or deprotect the oligonucleotide, the anhydrous amine reagent can be introduced and used under conditions suitable to further cleave or deprotect the oligonucleotide. The amine reagent is removed as disclosed above by washing, aeration or any other means, with the oligonucleotide remaining on the support. The oligonucleotide can then be eluted from the support or used in situ.

A two step procedure such as this, with gas phase reagents used in combination with anhydrous amines, permits a combination of protecting groups to be used without the risk of unwanted modifications. For example, gas phase ammonia would remove sensitive protecting groups, particularly the classical protecting group on cytosine in the form of a benzoyl group, but would not modify such a benzoyl C ($C^{Bz}$).

After the initial removal of this relatively unstable C protecting group an anhydrous amine reagent can be used in either the solution or gas phase to complete the cleavage or deprotection of the oligonucleotide without dissolving it from the support. The combination of reagents with gas phase and liquid anhydrous phase would allow the reactions to proceed at higher speed without the need for heating the solution or gas. The removal of substantially all benzoyl groups on $C^{Bz}$ can be achieved at room temperature using ammonia gas at 120 psi in 20 minutes. The removal of all the residual protecting groups on the oligonucleotide, when protected with regular protecting groups, ($C^{Bz}$, $A^{Bz}$, $G^{iBu}$) can be achieved at room temperature within 90 minutes.

The method of this invention offers new opportunities for the chemical modification of DNA and RNA molecules. The use of the technique for custom synthesis using pmolar amounts can reduce the cost of present technology more that 10 fold. The method of this invention also finds particular applications in such areas as Good Manufacturing Practice ("GMP"), as promulgated by the Food and Drug Administration for drug manufacturing procedures. For instance, the method lends itself well to the manufacture of antisense DNA and RNA, as well as diagnostic kits using oligonucleotide probes, diagnostic kits that rely on the amplification of small or infrequent gene sequences underlying genetic defects and infectious diseases.

The present invention will be further understood in view of the following Examples, which are provided to illustrate the invention, but are not intended to be comprehensive or limiting in any way.

EXAMPLES

Example 1

Anhydrous Amine Reagent Used Neat

A preferred method of the present invention is performed in the following manner. An oligonucleotide (e.g., 20–30 nucleotides in length) is synthesized with Expedite™ (PerSeptive Biosystems, Natick, Mass.) phosphoramidite monomers on a 0.2 micromolar (controlled pore glass, CPG) oligonucleotide synthesis column. The Expedite™ chemistry, (tert-butyl)phenoxyacetyl, protected cyanoethylphosphoramidites of $A^{BPA}$, $C^{BPA}$, $G^{BPA}$ and T, is performed on a "BioSearch 8750" oligonucleotide synthesizer using a standard manufacturing protocol for Expedite™ oligonucleotide synthesis. Upon completion of the synthesis the column is separately treated by incubation (15 min, ambient temperature) with 0.5 ml liquid hexylamine added to the column using a syringe. The hexylamine is removed from the column by the elution with tetrahydrofuran (THF) in an other syringe (3 ml).

The THF is removed and the column is then dried using a male Luer connector connected to a diaphragm pump sufficient to pull air through the column for 5 minutes (e.g., at a rate of 50 ml/min.). The oligonucleotide product is eluted with 1 ml of water. The optical density at 260 nm is estimated to be about 20 O.D. As a control, the same oligonucleotide is made by the same chemicals and cleaved and deprotected using standard ammonium hydroxide protocol for 16 h at 55° C. overnight. The solution is concentrated and the oligonucleotide taken up in water. The optical density reading at 260 nm corresponded is then determined.

Gel electrophoresis on polyacrylamide of both samples is performed, to determine whether both show the same retention time when illuminated with U.V light in the presence of ethidium bromide.

Example 2

Anhydrous Amine/Solvent Combination

Rather than hexylamine, a 20/30-mer as described in Example 1 is treated with propylamine/THF (1:1 by volume, 0.5 ml) in a synthetic column for 10 minutes at room temperature. The amine mixture is then removed by a THF (3 ml) wash. The column is then dried with air flow for 5 minutes and the oligonucleotide is eluted with 1 ml of water. The optical density at 260 nm is then determined, and the product is confirmed to have the same electrophoretic mobility as the reference sample.

These Examples 1 and 2 demonstrate the manner in which cleavage and deprotection using primary amines at room temperature can be fast using a two phase system of solid phase - liquid phase reaction.

Example 3

Microtiter Well Format

A 96 well microtiter plate is used for oligonucleotide synthesis and recovery in the following manner.

1. Each well of the plate is fitted with a DNA synthesis loose support material in combination with means for retaining the support material in the well. Optionally, the microplate can contain loose support material on top a the depth filter of have loose support between two depth filters or have inclusions of support in a depth filter or a frit. The support material is typically CPG, polystyrene, PVDF disk membranes. A membrane can also serve as a frit or filter for the plate. Conventional support material (e.g., CPG or polystyrene) having the first nucleoside covalently attached.
2. The microplate is placed in a chamber capable of holding an inert gas to protect the chamber from the ambient environment. The 5'-hydroxyl group is protected with a protecting group (typically DMT), which can be removed during synthesis, leaving the 5'-position available for coupling to another nucleotide.
3. A solvent such as acetonitrile is introduced in the well for washing the resin. After washing, the solvent is removed from the well by any suitable means, e.g., using pressure in the chamber or vacuum or centrifugal force to remove the solvent.
4. The protecting group of the nucleoside or nucleotide bound to the support is removed by adding a suitable reagent. Typically this reagent is 2% dichloroacetic acid in dichloromethane, when a DMT protecting group is used. The deprotection reaction is allowed to go to completion (generally about 15 to 60 seconds) and can be repeated if necessary. The emptying is performed as in step 3.
5. A washing procedure is followed using conventional techniques, typically using acetonitrile or any other suitable solvent, followed again by an emptying step.
6. A reactive nucleoside or nucleotide derivative or monomer is introduced in preactivated form, or activation can be done in the well. Typically, a DMT-nucleotide (A,C, G,T) is protected at its side chain in the form of a base labile acetyl, benzoyl or phenoxyacetyl derivative, or an amidine derivative.
7. The reaction mixture is kept in the well for a short period, typically between 5 to 200 seconds, as deemed necessary for the reaction conditions used. The mixture can be agitated to improve the distribution of reagents, followed by emptying and washing procedures as described above.
8. Finally, the internucleotide phosphite bond is oxidized to a stable phosphate triester.
9. Following oxidation, the well contents are washed and the wells emptied as before, before the capping reaction of nonreacted 5'-hydroxyl groups. The capping can be performed with suitable reagents for the inactivation (capping) of nonreacted groups for non-participation in the next cycle.
10. Steps 3 through 9 are then repeated for each subsequent cycle.
11. The procedure described above is repeated until the final product has been synthesized. Typically, the oligonucleotide can be synthesized in varying sizes of from about 5 nucleotides to over 100 nucleotides.
12. At the completion of synthesis, the recovery (e.g., cleavage and deprotection) steps described herein are performed using a suitable anhydrous amine reagent according to the method described in Examples 1 or 2. The elution of the final cleaved, deprotected oligonucleotide product from the microplate is accomplished by centrifugation, pressure, or gravity flow, with the product collected into separate tubes. Optionally, the oligonucleotide can be purified on the synthetic resin itself, e.g., if the resin is sufficiently hydrophobic, using a cartridge purification procedure as described in Examples 4 or 5. When recovered in the form of an ammonium salt, the product can also optionally be converted to a nontoxic sodium salt in the manner described above.

Finally, in lieu of particulate support material, it can be advantageous to purify small amounts of oligonucleotide on membranes having affinity for the oligonucleotide. After affinity chromatography, such oligonucleotides can be eluted with appropriate solutions and subsequently used in molecular biology applications.

Example 4

Integrated Cartridge Purification and Anhydrous Amine Cleavage

DMT-oligonucleotide purification can be performed in an automated fashion using an oligonucleotide synthesizer, or by manual means using syringes and conventional oligonucleotide synthesis columns. Conventional oligonucleotide synthesis columns typically have the support material retained withing a cylindrical or conical column that provides Luer or other fittings at its ends, for use in attaching the columns to a oligonucleotide synthesizer. Optionally, the support material can be retained in a well or other tube or column, with or without a depth filters or frits for the microtiter plate synthesis format.

The anhydrous amine reagent is delivered to the column and there incubated with the support material under conditions (e.g., time and temperature) sufficient to cleave and/or deprotect the oligonucleotide. The amine reagent is then washed off using a solvent that does not substantially remove the cleaved, deprotected DMT-oligonucleotide from the support, and failure sequences are removed (e.g., by the use of 1–5% aqueous acetonitrile). The DMT-group is then removed, for example, with 1–2% trifluoroacetic acid in water, followed by a water wash. The fully deprotected oligonucleotide is then eluted with 5–20% acetonitrile in water and collected in a vial. The solution can be quantified using U.V. spectroscopy measurements at 260/280 nm. Evaporation and resuspension in water yields a purified, quantified user ready oligonucleotide for molecular biology applications.

Example 5

Integrated Desalting Procedure and Anhydrous Amine Cleavage

The method and reagents of the present invention permit newly synthesized oligonucleotides to be desalted, either in an automated fashion using a oligonucleotide synthesizer, or by manual means using syringes and conventional oligonucleotide synthesis columns. The oligonucleotide is synthesized on a support such as CPG (controlled pore glass), glass beads, polystyrene or PVDF. The oligonucleotide is then fully deprotected oligonucleotide using an anhydrous amine reagent of the present invention. Free residues of the protecting groups, including mixtures of amides from the deprotection step, are typically soluble in the amine reagent or the solvent used for removing the amine reagent, and are thus also washed off the column in the process.

The final rinse of the resin, and optional drying by gas, therefore provides the newly synthesized oligonucleotide in essentially "desalted" condition on the support. Following elution, the oligonucleotide is optionally quantified and used directly in molecular biology experiments. Desalting in this manner is preferred since such organic residues may interact with enzymes, and in turn, lower the efficiency and reactivity of enzymes used for sequencing, ligations, phosphorylation, and/or kination of the oligonucleotide.

Example 6

Synthesizer Application

Fully deprotected DNA on CPG column. In this configuration the final product is desalted with the column still on the synthesizer. The product is eluted into a vial, ready to be used in molecular biology experiments (after quantification by O.D.).

An ancillary container for use on a synthesizer (e.g., a container such as that typically filed with an ammonia cleavage reagent) is filled instead with anhydrous amine reagent (e.g., THF/hexylamine 1:1). If the synthesis column is itself of a type that cannot hold a sufficient volume of solutions, one can use the reagent in more concentrated (less diluted) form in order to sufficiently wet the support, or optionally, can use a higher concentration of amine in the solvent carrier. A second ancillary container can be filled with water. The automated synthesizer can be programmed according to the procedure below.

The desired oligonucleotide is synthesized on CPG support with DMT off, using conventional techniques. Following the final acetonitrile wash, and gas purging, the anhydrous amine is added in order to both rinse the column and fill the column, since the reaction will typically occur quickly upon addition of the reagent. For this reason, it is preferred that the reagent not be flushed through the system in undue amounts, since the partially deprotected DNA may be slightly soluble. The reagent is allowed to incubate in the column, e.g., for on the order of 15 minutes (at room temperature) if each of the nucleotides are protected by phenoxyacetyl groups, and for on the order of 60 to 90 minutes (at room temperature) if regular protecting groups are used on A and G, such as benzoyl and isobutyryl, respectively, and phenoxyacetyl is used to protect C.

The anhydrous amine reagent is removed by gas purging followed with an acetonitrile wash. The DNA is desalted at this stage since the protecting groups that are converted to amides are soluble in the reagent or acetonitrile. Remove the acetonitrile by gas purging if the oligonucleotide is not being evaporated after the elution. Elute by adding purified water slowly to the cartridge, transferring the eluate into a receiving vial. If the elution is done over 5–10 minutes, the oligonucleotide will be eluted in as little as 100 microliter.

What is claimed is:

1. A method for recovering synthesized oligonucleotides from a solid support, the method comprising the steps of: (1) providing a solid synthetic support having synthesized oligonucleotides bound thereto, and (2) incubating the solid support with an anhydrous amine reagent in an organic solvent solution under conditions suitable to cleave and deprotect the oligonucleotide, and (3) removing the solution phase reagent in a manner that substantially removes free residues of cleaved protecting groups and permits the cleaved and deprotected oligonucleotide to be preferentially retained on the support.

2. A method according to claim 1 comprising the further step of washing the support under conditions suitable to remove the reagent with the oligonucleotide retained on the support.

3. A method according to claim 1 comprising the further step of recovering the oligonucleotide from the support.

4. A method according to claim 1 comprising the further step of using the recovered oligonucleotide in situ.

5. A method according to claim 1 wherein the reagent is selected from the group consisting of primary alkylamines, secondary amines, and cyclic amines, as well as combinations thereof.

6. A method according to claim 5 wherein the reagent comprises a primary alkylamine selected from the group consisting of methylamine, ethylamine, propylamine, butylamine, pentylamine, hexylamine, heptylamine, and isomers thereof.

7. A method according to claim 5 wherein the reagent comprises a secondary amines selected from the group consisting of dimethylamine, ethylmethylamine, diethylamine, methylisopropylamine, and diisopropylamine.

8. A method according to claim 5 wherein the reagent comprises a cyclic amine selected from the group consisting of ethyleneimine, pyrrole, pyrrolidine, cyclohexylamine, benzylamine, and substituted derivatives thereof.

9. A method according to claim 5 wherein the reagent further comprises a nonpolar organic solvent.

10. A method according to claim 9 wherein the solvent is selected from the group consisting of tetrahydrofuran and acetonitrile.

11. A composition comprising a solid support and a cleaved, deprotected synthetic oligonucleotide thereon, wherein the oligonucleotide has been cleaved and deprotected by incubating the solid support with an anhydrous amine reagent in an organic solvent solution under conditions suitable to cleave and deprotect the oligonucleotide, and wherein the solution phase reagent has been removed in a manner that substantially removes free residues of cleaved protecting groups and permits the cleaved and deprotected oligonucleotide to be preferentially retained on the support.

12. A composition according to claim 11 wherein the amine reagent is selected from the group consisting of primary alkylamines, secondary amines, and cyclic amines, as well as combinations thereof.

13. A composition according to claim 12 wherein the amine reagent comprises a primary alkylamine selected from the group consisting of methylamine, ethylamine, propylamine, butylamine, pentylamine, hexylamine, heptylamine, and isomers thereof.

14. A composition according to claim 12 wherein the reagent comprises a secondary amines selected from the group consisting of dimethylamine, ethylmethylamine, diethylamine, methylisopropylamine, and diisopropylamine.

15. A composition according to claim 12 wherein the reagent comprises a cyclic amine selected from the group consisting of ethyleneimine, pyrrole, pyrrolidine, cyclohexylamine, benzylamine, and substituted derivatives thereof.

16. A composition according to claim 12 wherein the reagent further comprises a nonpolar organic solvent.

17. A composition according to claim 16 wherein the solvent is selected from the group consisting of tetrahydrofuran and acetonitrile.

18. A method according to claim 1 wherein the support is selected from the group consisting of controlled pore glass and polystyrene.

19. A composition according to claim 11 wherein the support is selected from the group consisting of controlled pore glass and polystyrene.

* * * * *